United States Patent
Cerny et al.

(10) Patent No.: US 10,220,146 B2
(45) Date of Patent: Mar. 5, 2019

(54) ADJUSTMENTS TO POSTURE STATE DEFINITION

(71) Applicant: Medtronic, Inc., Minneapolis, MN (US)

(72) Inventors: Douglas S. Cerny, Minneapolis, MN (US); Debbie A. McConnell, Edina, MN (US); Michael E. Newell, White Bear Lake, MN (US); Raj Mehra, Savage, MN (US)

(73) Assignee: Medtronic, Inc., Minneapolis, MN (US)

( * ) Notice: Subject to any disclaimer, the term of this patent is extended or adjusted under 35 U.S.C. 154(b) by 593 days.

(21) Appl. No.: 14/859,045

(22) Filed: Sep. 18, 2015

(65) Prior Publication Data

US 2017/0080151 A1  Mar. 23, 2017

(51) Int. Cl.
*A61N 1/36* (2006.01)
*A61M 5/172* (2006.01)
*G06F 19/00* (2018.01)

(52) U.S. Cl.
CPC ....... *A61M 5/1723* (2013.01); *A61N 1/36139* (2013.01); *G06F 19/34* (2013.01); *A61M 2230/005* (2013.01); *A61M 2230/62* (2013.01)

(58) Field of Classification Search
None
See application file for complete search history.

(56) References Cited

U.S. PATENT DOCUMENTS

| | | | |
|---|---|---|---|
| 5,040,534 A | 8/1991 | Mann et al. | |
| 6,044,297 A | 3/2000 | Sheldon et al. | |
| 8,165,840 B2 | 4/2012 | Hatlestad et al. | |
| 8,688,225 B2 | 4/2014 | Panken et al. | |
| 9,327,070 B2 * | 5/2016 | Skelton | A61M 5/14276 |
| 9,744,365 B2 * | 8/2017 | Davis | A61N 1/37247 |
| 9,814,887 B2 * | 11/2017 | Nikolski | A61N 1/36542 |
| 2010/0010383 A1 * | 1/2010 | Skelton | A61B 5/103 600/587 |
| 2010/0010391 A1 * | 1/2010 | Skelton | A61B 5/1116 600/595 |
| 2010/0010585 A1 * | 1/2010 | Davis | A61B 5/1116 607/62 |
| 2010/0280417 A1 * | 11/2010 | Skelton | A61M 5/14276 600/595 |

(Continued)

*Primary Examiner* — Sean Dougherty
(74) *Attorney, Agent, or Firm* — Shumaker & Sieffert, P.A.

(57) ABSTRACT

Devices, systems, and techniques for adjusting posture state definitions used to determine a posture state of a patient are described. In one example, a system may include an external programmer that includes a user interface configured to present an indication of a first posture state determined from the data representative of the patient posture during the period of time and a set of posture state definitions that at least partially define a plurality of posture states. The external programmer may also include a processor configured to receive an adjustment input from a user that requests an adjustment to the set of posture state definitions and obtain a second posture state, the second posture state determined from the data representative of the patient posture during the period of time and the adjusted set of posture state definitions. The user interface presents an indication of the second posture state.

23 Claims, 11 Drawing Sheets

(56) References Cited

U.S. PATENT DOCUMENTS

| | | | |
|---|---|---|---|
| 2010/0280579 A1* | 11/2010 | Denison | A61N 1/36082 607/62 |
| 2011/0172562 A1* | 7/2011 | Sahasrabudhe | A61B 5/0476 600/587 |
| 2011/0172564 A1* | 7/2011 | Drew | A61B 5/061 600/587 |
| 2011/0270134 A1* | 11/2011 | Skelton | A61N 1/36514 600/595 |
| 2013/0207889 A1 | 8/2013 | Chang et al. | |
| 2014/0058289 A1* | 2/2014 | Panken | G16H 50/20 600/595 |
| 2014/0074431 A1 | 3/2014 | Modi | |

* cited by examiner

ADJUSTMENTS TO POSTURE STATE DEFINITION

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure is directed to devices, systems, and techniques for adjusting posture state definitions used to determine a posture state of a patient. A medical device or system (e.g., an implantable medical device) may determine which posture state a patient has assumed in order to monitor patient activity and/or provide posture state-responsive therapy. The posture state definitions that define each posture state of a plurality of posture states may need to be calibrated or adjusted such that the postures assumed by the patient are accurately reflected by the posture states determined by the system.

For example, a programmer for a medical device may present an indication of a determined posture state for a patient during a period of time. If the patient or another user (e.g., a clinician) identifies the determined posture as not accurately representing the posture state actually assumed by the patient, the programmer may receive an adjustment input from the user that requests an adjustment to the set of posture state definitions previously used to determine the posture state. The programmer may then obtain an updated posture state using the adjusted set of posture state definitions and the previously acquired data. In this manner, the user may adjust the posture state definitions until the determined posture state is an accurate reflection of the posture assumed by the patient. This adjustment may be performed without requiring the patient to repeat the posture after each adjustment to the posture state definitions.

In one example, the disclosure describes a method that includes presenting, by a programmer for an implantable medical device (IMD), an indication of a first posture state determined from data representative of a patient posture during a period of time and a set of posture state definitions that at least partially define a plurality of posture states, wherein the first posture state is one posture state of the plurality of posture states, receiving, by the programmer, an adjustment input from a user that requests an adjustment to the set of posture state definitions, obtaining, by the programmer, a second posture state, the second posture state determined from the data representative of the patient posture during the period of time and the adjusted set of posture state definitions, and presenting, by the programmer, an indication of the second posture state.

In another example, the disclosure describes an external programmer for programming an implantable medical device (IMD), the external programmer including a user interface configured to present an indication of a first posture state determined from data representative of a patient posture during a period of time and a set of posture state definitions that at least partially define a plurality of posture states, wherein the first posture state is one posture state of the plurality of posture states, and a processor configured to receive an adjustment input from a user that requests an adjustment to the set of posture state definitions, and obtain a second posture state, the second posture state determined from the data representative of the patient posture during the period of time and the adjusted set of posture state definitions, wherein the user interface is configured to present an indication of the second posture state.

In another example, the disclosure describes a system that includes an implantable medical device (IMD) comprising one or more posture sensors configured to generate data representative of a patient posture during a period of time, and an external programmer for programming the IMD, the external programmer comprising, a user interface configured to present an indication of a first posture state determined from the data representative of the patient posture during the period of time and a set of posture state definitions that at least partially define a plurality of posture states, wherein the first posture state is one posture state of the plurality of posture states, and a processor configured to receive an adjustment input from a user that requests an adjustment to the set of posture state definitions, and obtain a second posture state, the second posture state determined from the data representative of the patient posture during the period of time and the adjusted set of posture state definitions, wherein the user interface is configured to present an indication of the second posture state.

In another example, the disclosure describes a system that includes means for presenting an indication of a first posture state determined from data representative of a patient posture during a period of time and a set of posture state definitions that at least partially define a plurality of posture states, wherein the first posture state is one posture state of the plurality of posture states, means for receiving an adjustment input from a user that requests an adjustment to the set of posture state definitions, means for obtaining a second posture state, the second posture state determined from the data representative of the patient posture during the period of time and the adjusted set of posture state definitions, and means for presenting an indication of the second posture state.

In another example, the disclosure describes a computer-readable medium including instructions that, when executed by a processor, cause the processor to present, via a user interface of a programmer, an indication of a first posture state determined from data representative of a patient posture during a period of time and a set of posture state definitions that at least partially define a plurality of posture states, wherein the first posture state is one posture state of the plurality of posture states, receive an adjustment input from a user that requests an adjustment to the set of posture state definitions, obtain a second posture state, the second posture state determined from the data representative of the patient posture during the period of time and the adjusted set of posture state definitions, and present, via the user interface, an indication of the second posture state.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1A:
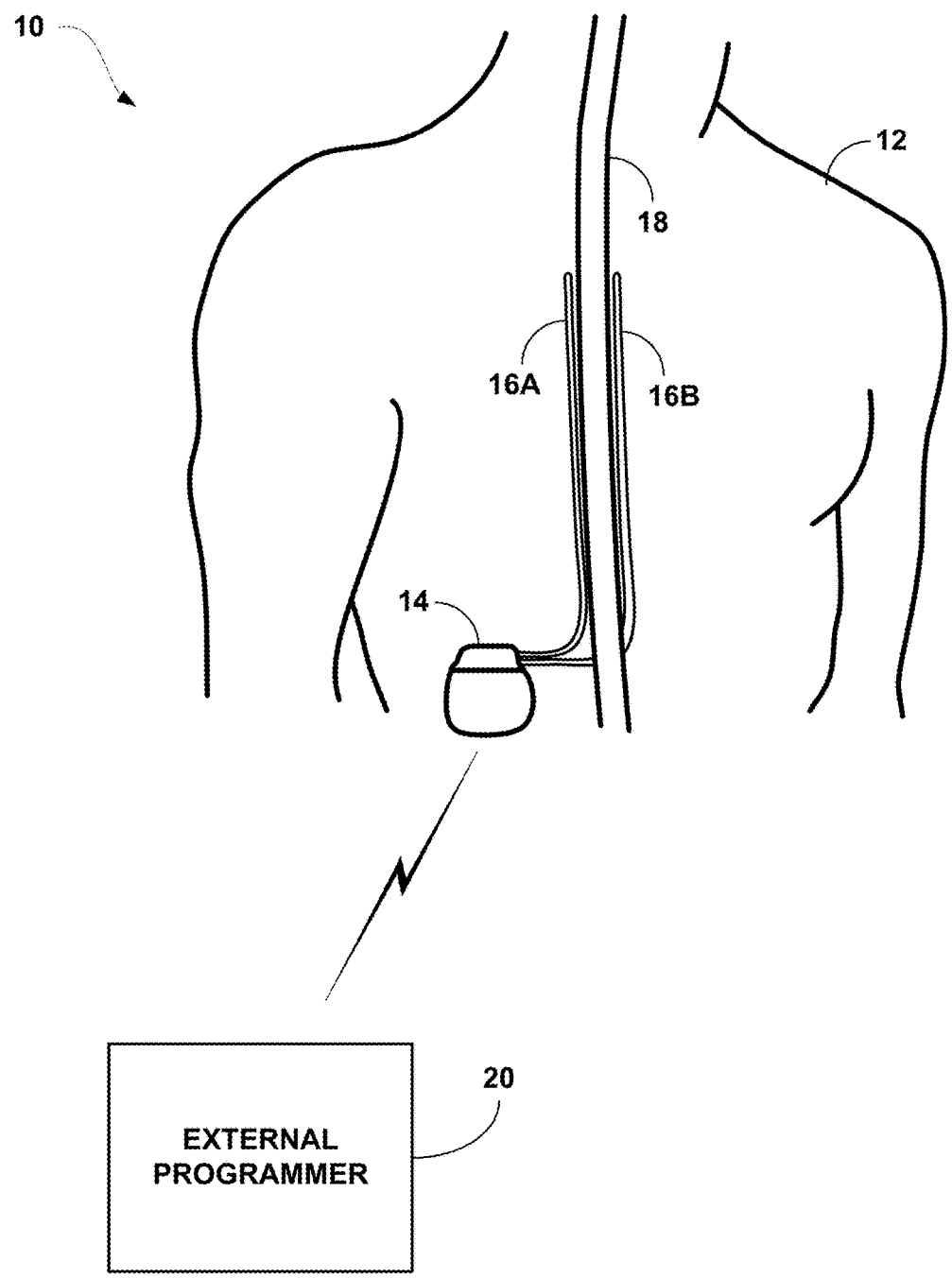
FIG. 1A is a conceptual diagram illustrating an implantable stimulation system including two implantable stimulation leads.

In general, the disclosure is directed to devices, systems, and techniques for adjusting posture state definitions used to determine a posture state of a patient. In some medical devices that deliver electrical stimulation therapy, therapeutic efficacy may change as the patient changes posture states. In general, a posture state may refer to a posture, an activity, or a combination of posture and activity. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. For example, for a given patient, sitting may be more painful on the patient's back than standing regardless of any migration or compression of the therapy delivery elements. To maintain therapeutic efficacy, it may be desirable to adjust therapy parameters based on different postures and/or activities engaged by the patient to maintain effective stimulation therapy. Therapy parameters may be adjusted directly or by selecting different programs or groups of programs defining different sets of therapy parameters.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device may employ a posture state detector that detects the patient posture state. The medical device may adjust therapy parameters in response to different posture states as detected by the posture state detector. For posture state-responsive therapy, therapy adjustments in response to different posture states may be fully automatic (e.g., the system provides posture-responsive therapy without any user input) or semi-automatic (e.g., a user may provide approval of system-proposed changes).

Posture states may be detected by one or more sensors in a medical device. After implantation or attachment to the patient, the posture sensors need to be calibrated or adjusted to their specific orientation in the patient and/or the manner in which the specific patient performs actions. Calibration may involve asking the patient to assume each different posture state and have the medical device associate those posture states with the data generated from the posture sensors at the time each posture state was assumed by the patient. In some examples, the parameters, or boundaries, of each posture state as defined by the set of posture state definitions may need to be adjusted or modified to improve the accurate of posture state detection.

However, this process may involve trial and error as the patient or the clinician adjusts a parameter, instructs the patient to assume the posture state again, and the system outputs the newly detected posture state. This process may continue over many iterations until the patient or clinician can dial into the most appropriate parameter value for the set of posture state definitions. The process can become even more time consuming for posture states that require a longer duration of time for the system to establish a steady state. For example, a mobile posture state may be a posture state in which accelerations are detected that indicate the patient is walking, running, or otherwise active (as opposed to stationary). This inefficient process may require a greater amount of physician time. In addition, a patient may become fatigued from repeating the mobile posture state over time such that subsequent iterations of the posture state are less representative of a real-life mobile posture state.

As described herein, a system may facilitate the adjustment of posture state definitions by providing feedback regarding how the adjustment would affect the determination of posture states using the same sensor data. In other words, the system may indicate which posture states would be determined from data using the adjusted posture state definitions instead of the previous posture state definitions.

In addition, the system may provide user interface tools that guide the user through these adjustments.

In one example, a programmer may present an indication of a determined posture state for a patient during a period of time. If the patient or another user (e.g., a clinician) identifies the determined posture as not accurately representing the posture state actually assumed by the patient, the programmer may receive an adjustment input from the user that requests an adjustment to the set of posture state definitions previously used to determine the posture state. In some examples, the adjustment input may be provided via an adjustment mechanism (e.g., a slider or dial) provided by a user interface of the programmer. The programmer may then obtain an updated posture state using the adjusted set of posture state definitions and the previously acquired data. In this manner, the user may adjust the posture state definitions until the determined posture state is an accurate reflection of the posture actually assumed by the patient. This adjustment may be performed without requiring the patient to repeat the posture after each adjustment to the posture state definitions.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for SCS, e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). Although two leads are shown in FIG. 1A, a single lead or three or more leads may be used in other examples. Each lead may include the same number of electrodes or vary in the number and position of electrodes. In some applications, such as SCS to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 12 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that is used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry one or more arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 delivers stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program.

Moreover, therapy may be delivered according to multiple programs, wherein multiple programs are contained within each of a plurality of groups.

Each program group may support an alternative therapy selectable by patient 12, and IMD 14 may deliver therapy according to the multiple programs in a group. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. For example, stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. Additionally, in response to a posture state change, IMD 14 may communicate with external programmer 20 to provide a notification to a user, such a clinician, that patient 12 has potentially experienced a fall.

A user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

A user interface of external programmer 20 may indicate to the user the posture state in which the patient 12 currently resides. This patient posture state may be a static posture that does not take into account activity level (e.g., mobility), an activity level that does not take into account posture, or some combination of the posture and activity level that describes the physical position and movement (or mobility) of patient 12. As an example, posture may be characterized as one of the following posture states: standing, sitting, lying down on back, lying down on front, lying down on left side, and lying down on right side. Activity level, or mobility, may be characterized as one of high, medium and low, or be characterized in terms of a numeric scale, e.g., 1-10 or 1-12. In other examples, other gradations, e.g., high, medium high, medium, medium low, and low, or other numerical scales may be used to characterize activity level. Respective thresholds, or parameters, may be used in the posture state definitions to define each of these levels. Alternatively, a single mobility posture state may be used which indicates that the activity is above a certain threshold. The mobility posture state may be applicable regardless of the other static orientations also detected or only indicated when another posture is also detected (e.g., the mobility posture state may only be determined when the upright or standing posture is also detected).

A posture state may indicate a combination of one of the above postures with one of the above activity levels. For some postures, such as lying down postures, the posture state may not need to consider activity level, as the patient may be less likely to undertake any significant activity in such postures. In other cases, all posture states may take into account posture and activity level, even if there is minimal activity in a particular posture. Posture state may be determined based on posture information and/or activity level information generated by a posture state module, which may include one or more accelerometers or other posture or activity level sensors.

A patient posture state may be represented by a posture state indication presented by the user interface of programmer 20 as a visible, audible, or tactile indication. When presented as a visible indication, the posture state indication may be, for example, a graphical representation, a symbolic icon, a textual representation, such as word or number, an arrow, or any other type of indication. The visible indication may be presented via a display, such as an a liquid crystal display (LCD), dot matrix display, organic light-emitting diode (OLED) display, touch screen, or the like. In other cases, the visible indication may be provided in a translucent area that is selectively backlit to indicate a posture. An audible indication may be produced by programmer 20 as spoken words stating a posture state, or different audible tones, different numbers of tones, or other audible information generated by the programmer to indicate posture state. A tactile indication of posture state may be produced by programmer 20, for example, in the form of different numbers of vibratory pulses delivered in sequence or vibratory pulses of different lengths, amplitudes, or frequencies.

Programmer 20 may present multiple indications representative of different patient posture states. IMD 14 may communicate a patient posture state according to a posture state parameter value sensed by a posture state module (e.g., data generated by the module) to external programmer 20, e.g., by wireless telemetry. For example, IMD 14 may transmit a posture state indication to programmer 20 on a periodic, intermittent or continuous basis or in response to a posture state change. Alternatively, programmer 20 may request a posture state indication from IMD 14 on a periodic, intermittent or continuous basis. External programmer 20 then may select and present the associated posture state indication. In some examples, IMD 14 may transmit posture data to programmer 20, and programmer 20 may determine the posture states based on the posture data and posture state definitions.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use. The clinician programmer may be configured to control all features or aspects of therapy, while the patient programmer may have limited programming functionality (e.g., programming limited to certain features and/or limited as to the amount of adjustment the patient can make using the patient programmer).

A patient programmer or clinician programmer may is a hand held device. A clinician programmer may be used to communicate with multiple IMDs 14 (FIG. 1A) and 26 (FIG. 1B) within different patients. In this manner, clinician programmer may be capable of communicating with many different devices and retain patient data separate for other patient data. In some embodiments, the clinician programmer may be a larger device that may be less portable, such as a notebook computer, workstation, or even a remote computer that communicates with IMD 14 or 26 via a remote telemetry device.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
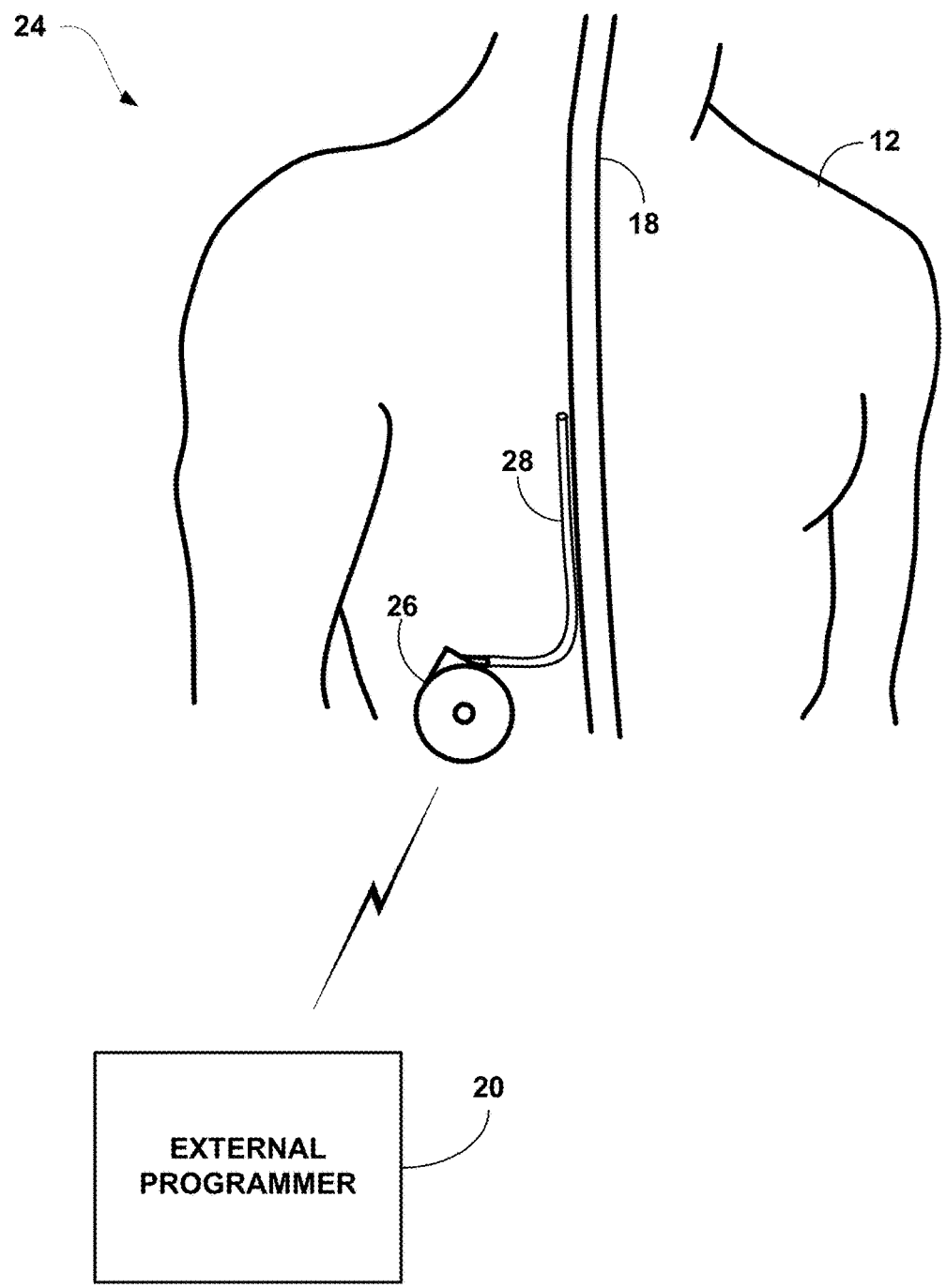
FIG. 1B is a conceptual diagram illustrating an implantable drug delivery system including a delivery catheter.

FIG. 1B is a conceptual diagram illustrating an implantable drug delivery system 24 including one delivery catheter 28 coupled to IMD 26. As shown in the example of FIG. 1B, drug delivery system 24 is substantially similar to system 10. However, drug delivery system 24 performs the similar therapy functions via delivery of drug stimulation therapy instead of electrical stimulation therapy. IMD 26 functions as a drug pump in the example of FIG. 1B, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that forms catheter 28 or that is coupled to catheter 28, e.g., via a fluid coupler. In other examples, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
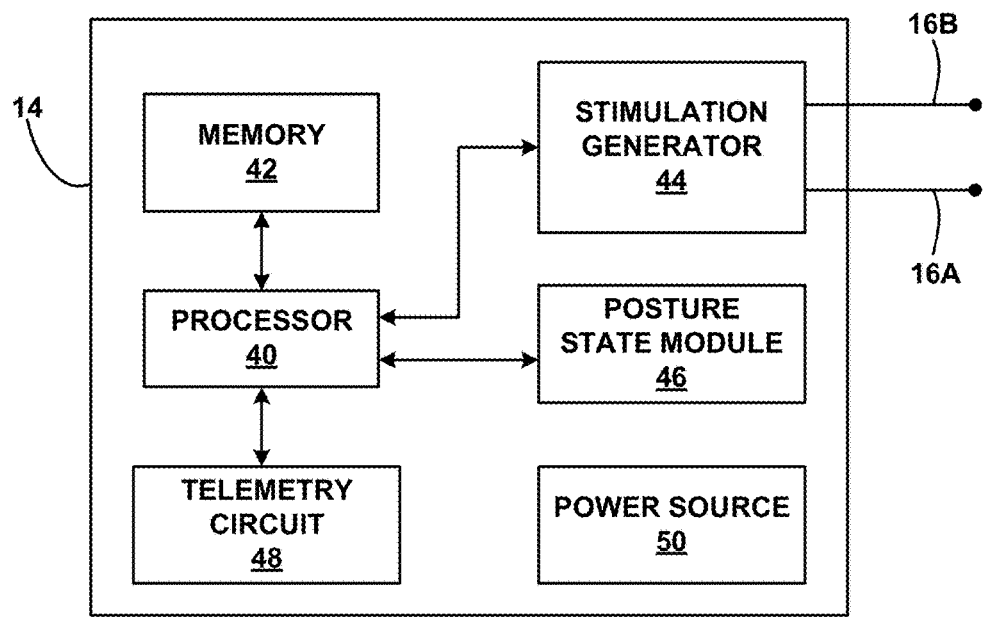
FIG. 2 is a functional block diagram illustrating various components of an implantable electrical stimulator.

FIG. 2 is a functional block diagram illustrating various components of an IMD 14. In the example of FIG. 2, IMD 14 includes a processor 40, memory 42, stimulation generator 44, posture state module 46, telemetry circuit 48, and power source 50. Memory 42 may store instructions for execution by processor 40, stimulation therapy data, posture state information, posture state indications, and any other information regarding therapy or patient 12. Therapy information may be recorded for long-term storage and retrieval by a user, and the therapy information may include any data created by or stored in IMD 14. Memory 42 may include separate memories for storing instructions, posture state information (e.g., sets of posture state definitions), program histories, and any other data that may benefit from separate physical memory modules.

Processor 40 controls stimulation generator 44 to deliver electrical stimulation via electrode combinations formed by electrodes in one or more electrode arrays. For example, stimulation generator 44 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 44 may include stimulation generation circuitry to generate stimulation pulses or waveforms and switching circuitry to switch the stimulation across different electrode combinations, e.g., in response to control by processor 40. In particular, processor 40 may control the switching circuitry on a selective basis to cause stimulation generator 44 to deliver electrical stimulation to selected electrode combinations and to shift the electrical stimulation to different electrode combinations in a first direction or a second direction when the therapy must be delivered to a different location within patient 12. In other embodiments, stimulation generator 44 may include multiple current or voltage sources to drive more than one electrode combination at one time. In this case, stimulation generator 44 may decrease a stimulation amplitude (e.g., a current or voltage amplitude) to the first electrode combination and simultaneously increase a stimulation amplitude to the second electrode combination to shift the stimulation therapy.

An electrode combination may be represented by a data stored in a memory location, e.g., in memory 42, of IMD 14. Processor 40 may access the memory location to determine the electrode combination and control stimulation generator 44 to deliver electrical stimulation via the indicated electrode combination. To change electrode combinations, current or voltage amplitudes, pulse rates, or pulse widths, processor 40 may command stimulation generator 44 to make the appropriate changes to therapy according to instructions within memory 42 and rewrite the memory location to indicate the changed therapy. In other examples, rather than rewriting a single memory location, processor 40 may make use of two or more memory locations.

When activating stimulation, processor 40 may access not only the memory location specifying the electrode combination but also other memory locations specifying various stimulation parameters such as voltage or current amplitude, pulse width and pulse rate. Stimulation generator 44, e.g., under control of processor 40, then makes use of the electrode combination and parameters in formulating and delivering the electrical stimulation to patient 12. Processor 40 also may control telemetry circuit 48 to send and receive information to and from external programmer 20. For example, telemetry circuit 48 may send information to and receive information from patient programmer 30. An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between 0.1 milliamps (mA) and 50 mA.

3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 40 stores stimulation parameters in memory 42, e.g., as programs and groups of programs. Upon selection of a particular program group, processor 40 may control stimulation generator 44 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads.

Posture state module 46 allows IMD 14 to sense the patient posture state, e.g., posture, activity or any other static position or motion of patient 12. In the example of FIG. 2, posture state module 46 may include one or more accelerometers, such as three-axis accelerometers, capable of detecting static orientation or vectors in three-dimensions. For example, posture state module 46 may include one or more micro-electro-mechanical accelerometers. In other examples, posture state module 46 may alternatively or additionally include one or more gyroscopes, pressure transducers or other sensors to sense the posture state of patient 12. Posture state information (e.g., posture data) generated by posture state module 46 and processor 40 may correspond to an activity and/or posture undertaken by patient 12 or a gross level of physical activity, e.g., activity counts based on footfalls or the like.

In some examples, processor 40 processes the analog output of the posture state sensor in posture state module 46 to determine activity and/or posture data. For example, processor 40 or a processor of posture state module 46 may process the raw signals provided by the posture state sensor to determine activity counts. In some examples, processor 40 may process the signals provided by the posture state sensor to determine velocity of motion information along each axis. In some examples, processor 40 may transmit the determined posture states and/or the raw posture data to another device, such as programmer 20.

In one example, each of the x, y, and z signals provided by the posture state sensor has both a DC component and an AC component. The DC components may describe the gravitational force exerted upon the sensor and may thereby be used to determine orientation of the sensor within the gravitational field of the earth. Assuming the orientation of the sensor is relatively fixed with respect to patient 12, the DC components of the x, y and z signals may be utilized to determine the patient's orientation within the gravitational field, and hence to determine the posture of the patient.

The AC component of the x, y and z signals may yield information about patient motion. In particular, the AC component of a signal may be used to derive a value for an activity describing the patient's motion. This activity may involve a level, direction of motion, or acceleration of patient 12.

One method for determining the activity is an activity count. An activity count may be used to indicate the activity or activity level of patient 12. For example, a signal processor may sum the magnitudes of the AC portion of an accelerometer signal for "N" consecutive samples. For instance, assuming sampling occurs as 25 Hz, "N" may be set to 25, so that count logic provides the sum of the samples that are obtained in one second. This sum may be referred to as an "activity count." In other examples, sampling may be conducted faster than 25 Hz (e.g., 50 Hz or greater) or much slower (e.g., less than 1 Hz or 0.5 Hz) and still capture patient activity (e.g., walking, standing, etc.).

The number "N" of consecutive samples may be selected by processor 40 or a processor of posture state module 46 based on the current posture state, if desired. The activity count may be the activity portion of the posture state parameter value that may be added to the posture portion. The resulting posture state parameter value may then incorporate both activity and posture to generate an accurate indication of the motion of patient 12.

As another example, the activity portion of the posture state parameter value may describe a direction of motion. This activity parameter may be associated with a vector and an associated tolerance, which may be a distance from the vector. Another example of an activity parameter relates to acceleration. A value quantifying a level of change of motion over time in a particular direction may be associated with the activity portion of a posture state parameter value. One or more parameters, e.g. a threshold, may be defined by the set of posture state definitions for determining when the activity arises to a certain posture state such as a mobile posture state. In some examples, the set of posture state definitions includes multiple posture state definitions. In other examples, the set of posture state definitions may only include a single posture state definition.

Posture state information from posture state module 46 may be stored in memory 42 for later review by a clinician, used to adjust therapy, present a posture state indication to patient 12 via programmer 20, or some combination thereof. As an example, processor 40 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture.

IMD 14 may also store which group or program was being used to deliver therapy when patient 12 was in the sensed posture. Further, processor 40 may also adjust therapy for a new posture when posture state module 46 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 46 that indicates the posture state may constantly vary throughout the day of patient 12. However, a certain activity (e.g., walking, running, or biking or other mobile event) or a posture (e.g., standing, sitting, or lying down) may include multiple posture state parameter values from posture state module 46. Memory 42 may include definitions for each posture state of patient 12. Together, these definitions may be described as a set of posture state definitions. In one example, the definitions of each posture state may be illustrated as a cone in three-dimensional space. Whenever the posture state parameter value, e.g., a vector, from the three-axis accelerometer of posture state module 46 resides within a predefined cone, processor 40 indicates that patient 12 is in the posture state of the cone. A cone is described for purposes of example. Other definitions of posture states may be illustrated as other shapes, e.g., donuts, in three-dimensional space. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of programmer 20 multiple times during the patient posture state to maintain adequate symptom control. In some examples, patient 12 may eventually be able to enjoy posture state responsive stimulation therapy without the need to continue making changes for different postures via programmer 20. Instead, patient 12 may transition immediately or over time to fully automatic adjustments based on posture state.

Although posture state module 46 is described as containing a 3-axis accelerometer, posture state module 46 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), on an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 46 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 40, in some examples, to confirm or reject changes in sensed posture state that may result from vibration, patient travel (e.g., in an aircraft, car or train), or some other false positive of posture state.

Wireless telemetry in IMD 14 with external programmer 20 or another device may be accomplished by radio frequency (RF) communication or proximal inductive interaction of IMD 14 with external programmer 20. Telemetry circuit 48 may send information to and receive information from external programmer 20 on a continuous basis, at periodic intervals, at non-periodic intervals, or upon request from the stimulator or programmer. To support RF communication, telemetry circuit 48 may include appropriate electronic components, such as amplifiers, filters, mixers, encoders, decoders, and the like.

Power source 50 delivers operating power to the components of IMD 14. Power source 50 may include a small rechargeable or non-rechargeable battery and a power generation circuit to produce the operating power. Recharging may be accomplished through proximal inductive interaction between an external charger and an inductive charging coil within IMD 14. As one example, external programmer 20 may include the charger to recharge power source 50 of IMD 14. Hence, the programmer and charger may be integrated in the same device. Alternatively, in some cases, a charger unit may serve as an intermediate device that communicates with both the IMD and the programmer. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 3:
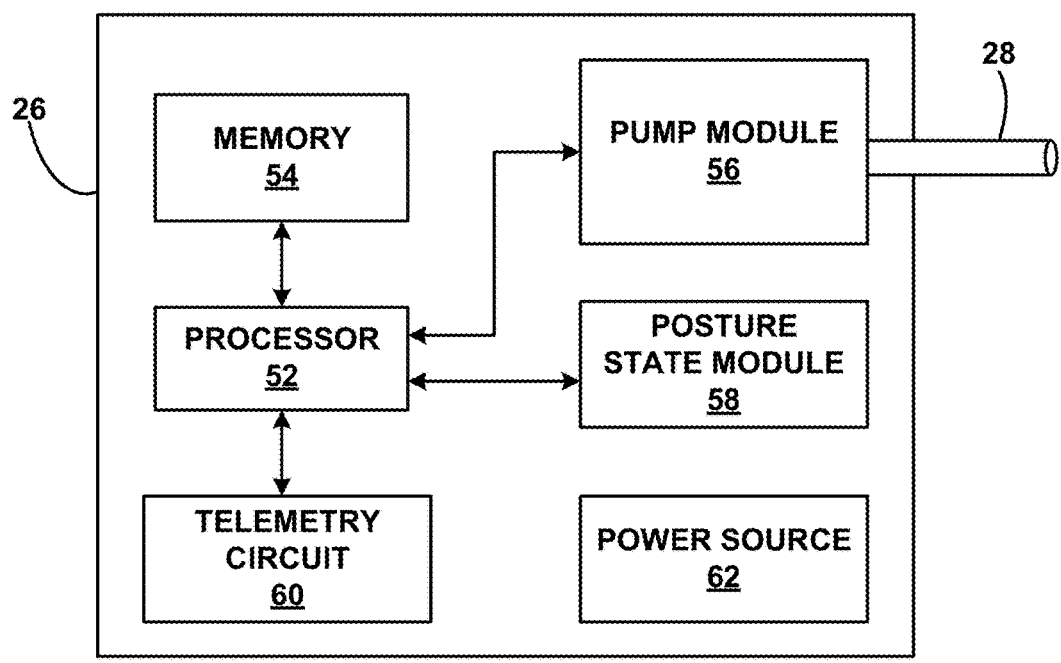
FIG. 3 is a functional block diagram illustrating various components of an implantable drug pump.

FIG. 3 is a functional block diagram illustrating various components of an IMD 26 that is a drug pump. IMD 26 is a drug pump that operates substantially similar to IMD 14 of FIG. 2. IMD 26 includes processor 52, memory 54, pump module 56, posture state module 58, telemetry circuit 60, and power source 62. Instead of stimulation generator 44 of IMD 14, IMD 26 includes pump module 56 for delivering drugs or some other therapeutic agent via catheter 28. Pump module 56 may include a reservoir to hold the drug and a pump mechanism to force drug out of catheter 28 and into patient 12.

Processor 52 may control pump module 56 according to therapy instructions stored within memory 54. For example, memory 54 may contain the programs or groups of programs that define the drug delivery therapy for patient 12. A program may indicate the bolus size or flow rate of the drug, and processor 52 may accordingly deliver therapy. Processor 52 may also use posture state information from posture state module 58 to adjust drug delivery therapy when patient 12 changes posture states, e.g., adjusts his (or her) posture.

Figure 4:
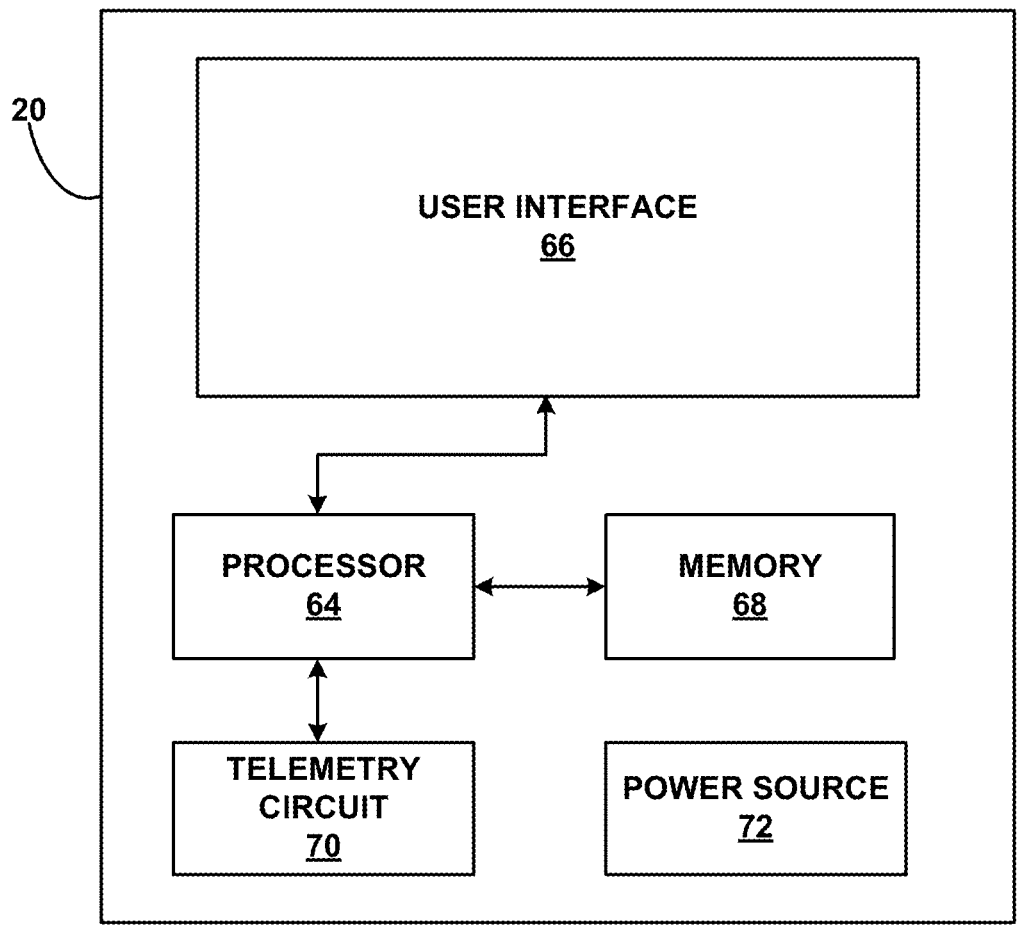
FIG. 4 is a functional block diagram illustrating various components of an external programmer for an implantable medical device.

FIG. 4 is a functional block diagram illustrating various components of an external programmer 20 for IMD 14 or 26. As shown in FIG. 4, external programmer 20 includes processor 64, memory 68, telemetry circuit 70, user interface 66, and power source 72. External programmer 20 may be embodied as a patient programmer or clinician programmer. A clinician or patient 12 interacts with user interface 66 in order to manually change the stimulation parameters of a program, change programs within a group, turn posture responsive therapy ON or OFF, adjust one or more parameters of the set of posture state definitions, view therapy information, view posture state information, or otherwise communicate with IMD 14 or 26.

User interface 66 may include a screen and one or more input buttons that allow external programmer 20 to receive input from a user. Alternatively, user interface 66 may additionally or only utilize a touch screen display. The screen may be a liquid crystal display (LCD), dot matrix display, organic light-emitting diode (OLED) display, presence sensitive display, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 66 may include a touch pad, increase and decrease buttons, emergency shut off button, and other buttons needed to control the stimulation therapy. Processor 64 controls user interface 66, retrieves data from memory 68 and stores data within memory 68. Processor 64 also controls the transmission of data through telemetry circuit 70 to IMD 14 or 26. Memory 68 includes operation instructions for processor 64 and data related to patient therapy. In this manner, user interface 66 may include one or more input devices that receive input from a user and one or more output devices that present information back to the user. In the example of a touch screen device, the touch screen device incorporates both a display as the output device and a touch sensitive (or presence sensitive) input device incorporated with the display. In other examples, user interface 66 may include separate input devices (e.g., buttons, keypads, switches dials, etc.) and one or more output devices (e.g., displays, lights, speakers, haptic devices, etc.).

Telemetry circuit 70 allows the transfer of data to and from IMD 14 or IMD 26. Telemetry circuit 70 may communicate automatically with IMD 14 at a scheduled time or when the telemetry circuit detects the proximity of the stimulator. Alternatively, telemetry circuit 70 may communicate with IMD 14 when signaled by a user through user interface 66. To support RF communication, telemetry circuit 70 may include appropriate electronic components, such as amplifiers, filters, mixers, encoders, decoders, and the like. Power source 72 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Figure 5:
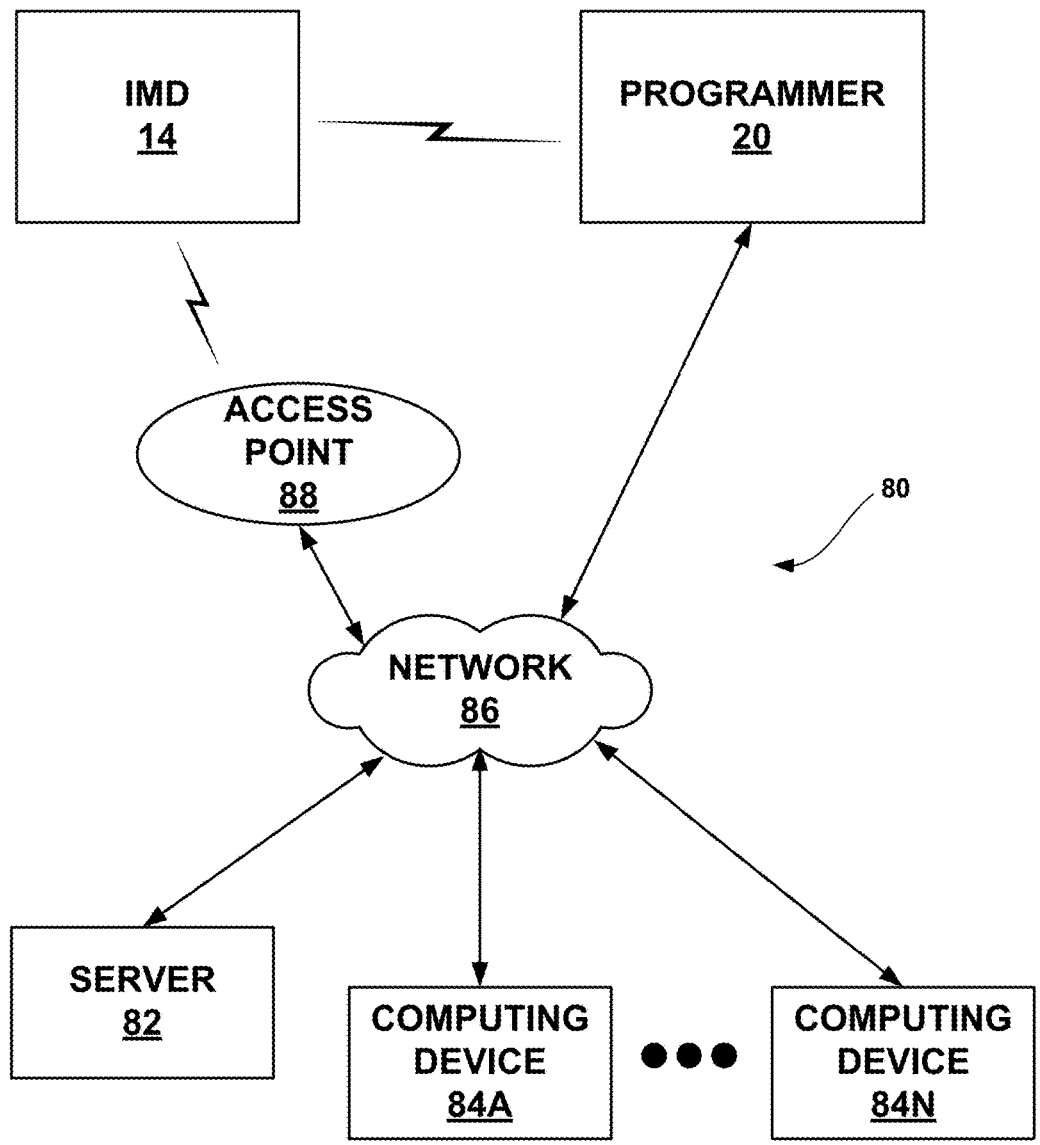
FIG. 5 is a block diagram illustrating an example system that includes an external device, such as a server, and one or more computing devices that are coupled to an implantable medical device and external programmer shown in FIGS. 1A and 1B via a network.

FIG. 5 is a block diagram illustrating an example system 80 that includes an external device, such as a server 82, and one or more computing devices 84A-84N, that are coupled to IMD 14 and external programmer 20 shown in FIGS. 1A-1B via a network 86. In this example, IMD 14 may use its telemetry circuit 88 to communicate with external programmer 20 via a first wireless connection, and to communicate with an access point 88 via a second wireless connection. In other examples, IMD 26 may also be used in place of IMD 14.

In the example of FIG. 5, access point 88, external programmer 20, server 82, and computing devices 84A-84N are interconnected, and able to communicate with each other, through network 86. In some cases, one or more of access point 88, external programmer 20, server 82, and computing devices 84A-84N may be coupled to network 86 through one or more wireless connections. IMD 14, external programmer 20, server 82, and computing devices 84A-84N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 88 may comprise a device, such as a home monitoring device, that connects to network 86 via any of a variety of connections, such as telephone dial-up, digital subscriber line (DSL), or cable modem connections. In other examples, access point 88 may be coupled to network 86 through different forms of connections, including wired or wireless connections.

During operation, IMD 14 may collect and store various forms of data. For example, IMD 14 may collect sensed posture state information during therapy delivery that indicate how patient 12 moves throughout each day. In some cases, IMD 14 may directly analyze the collected data to evaluate the patient 12 posture state, such as what percentage of time patient 12 was in each identified posture state. In other cases, however, IMD 14 may send stored data relating to posture state information to external programmer 20 and/or server 82, either wirelessly or via access point 88 and network 86, for remote processing and analysis. For example, IMD 14 may sense, process, trend and evaluate the sensed posture state information. Alternatively, processing, trending and evaluation functions may be distributed to other devices such as external programmer 20 or server 82, which are coupled to network 86. In addition, posture state information may be archived by any of such devices, e.g., for later retrieval and analysis by a clinician.

In some cases, IMD 14, external programmer 20 or server 82 may process posture state information or raw data and/or therapy information into a displayable posture state report, which may be displayed via external programmer 20 or one of computing devices 84A-84N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 82. A clinician or other trained professional may review and/or annotate the posture state report, and possibly identify any problems or issues with the therapy that should be addressed.

In some cases, server 82 may be configured to provide a secure storage site for archival of posture state information that has been collected from IMD 14 and/or external programmer 20. Network 86 may comprise a local area network, wide area network, or global network, such as the Internet. In some cases, external programmer 20 or server 82 may assemble posture state information in web pages or other documents for viewing by trained professionals, such as clinicians, via viewing terminals associated with computing devices 84A-84N. System 80 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 80 may be employed to distribute any information relating to the treatment of patient 12 and the operation of any device associated therewith. For example, system 80 may allow therapy errors or device errors to be immediately reported to the clinician. In addition, system 80 may allow the clinician to remotely intervene in the therapy and reprogram IMD 14, patient programmer 30, or communicate with patient 12. In an additional example, the clinician may utilize system 80 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that provide other therapy (e.g., drug pumps) or IMDs that are generally dedicated to sensing or monitoring and do not include stimulation or other therapy components.

Figure 6A:
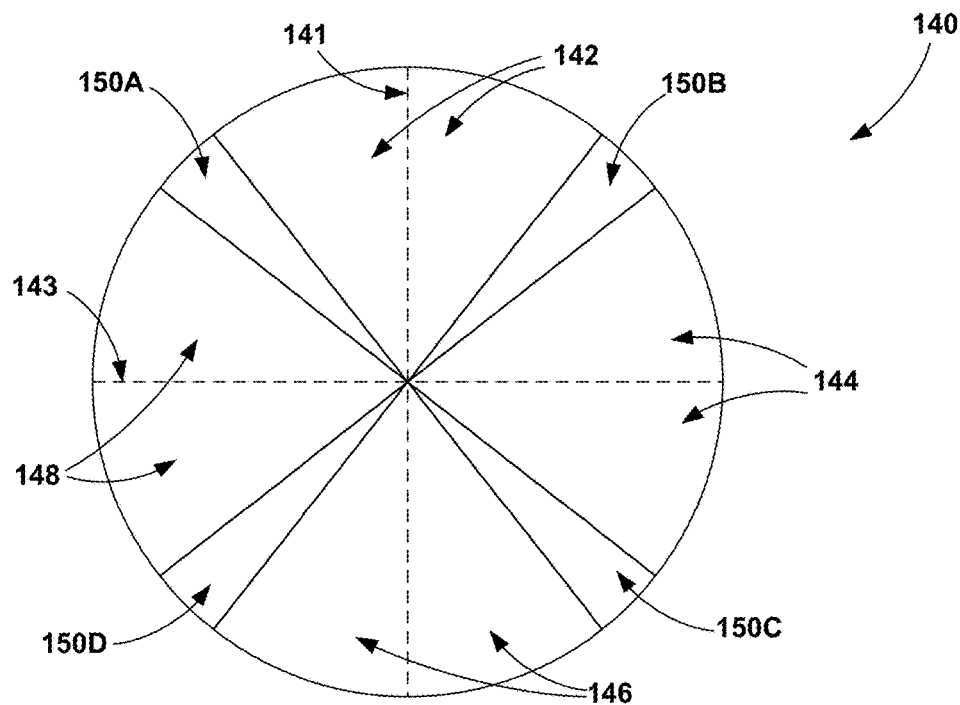
FIGS. 6A-6C are conceptual illustrations of example posture state spaces within which postures state reference data may define the posture state of a patient.
Figure 6B:
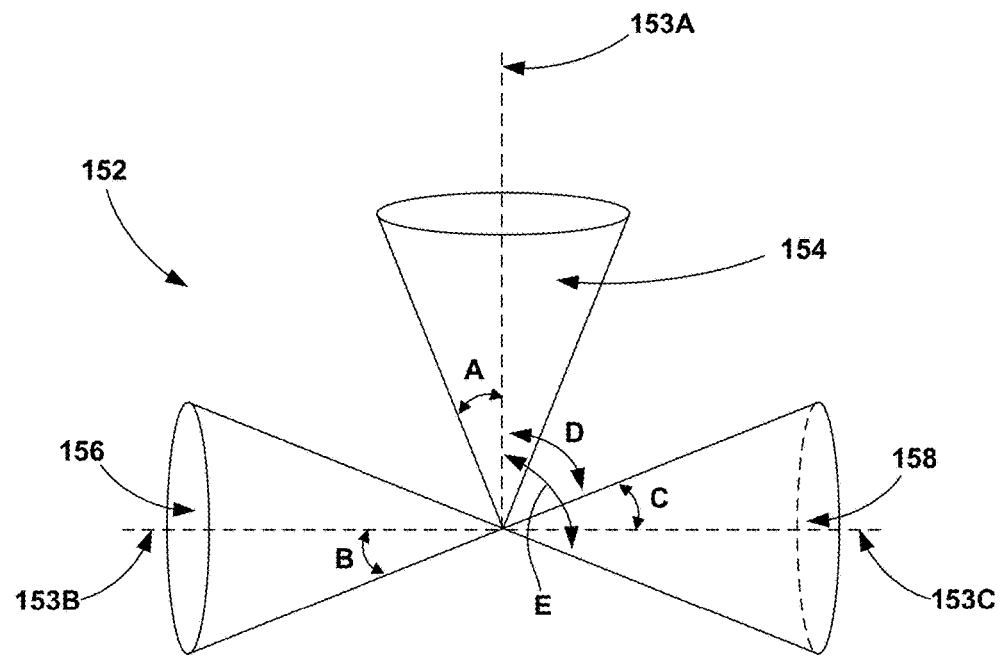
Figure 6C:
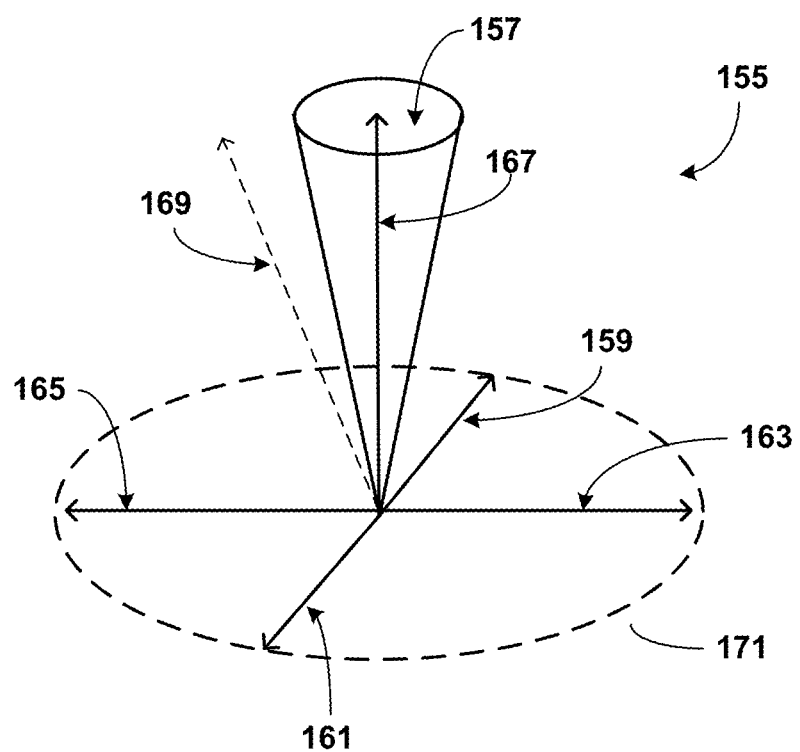

FIGS. 6A-6C are conceptual illustrations of posture state spaces 140, 152, 155, respectively, within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 46 with respect to posture state spaces 140, 152, 155 to determine the posture state of patient 12. For example, if the output of one or more posture state sensors is within a particular posture region defined by posture state reference data (i.e., one or more posture state definitions that define respective posture regions), posture state module 46 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 6A and 6B, the posture state module 46 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 6A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 6A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 6A. In particular, the lying right and lying left posture cones may be positioned in a coronal plane substantially perpendicular to the sagittal plane illustrated in FIG. 6A. For ease of illustration, lying right and lying left cones are not shown in FIG. 6A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 6A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 46 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to programmer 20 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 6A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively, or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 6A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. The reclining back posture may be spatially located between the lying back cone 148 and upright cone 142 in some examples. In other examples, posture state area 140 may include fewer posture cones than cones 142, 144, 146, 148 shown in FIG. 6A. For example, inverted cone 146 may be replaced by a larger lying back cone 148 and lying front cone 144.

FIG. 6B illustrates an example posture state space 152 that is a three-dimensional space in which the posture state parameter value from the posture state sensor is placed in relation to the posture cones. Posture state space 152 is substantially similar to posture state area 140 of FIG. 6A. However, the posture state parameter value derived from all three axes of a 3-axis accelerometer may be used to accurately determine the posture state of patient 12. In the example of FIG. 6B, posture state space 152 includes upright cone 154, lying back cone 156, and lying front cone 158. Posture state space 152 also includes hysteresis zones (not shown) similar to those of posture state area 140. In the example of FIG. 6B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 46 define a posture vector that corresponds to center line 153A.

The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 46, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 6B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 6B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 46 of IMD 14 when patient 12 occupies the respective postures.

In some cases, all of the posture cones may be individually defined based on actual reference coordinate vectors, where the reference coordinate vectors may be or included as part of one or more posture state definitions. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 46 of IMD 14 may determine a sensed coordinate vector based on the posture sensor data generated by one or more posture state sensors, and then analyze the sensed coordinate vector with respect to posture cones 154, 156, 158 of FIG. 6B. For example, in a case in which a posture cone is defined by a reference coordinate vector and a tolerance angle, e.g., tolerance angle "A," posture state module 46 may determine whether the sensed coordinate vector is within upright posture cone 154 by calculating the angle between the sensed coordinate vector and reference coordinate vector, and then determine whether the angle is less than the tolerance angle "A." If so, posture state module 46 determines that the sensed coordinate vector is within upright posture cone 154 and detects that patient 12 is in the upright posture. If posture state module 46 determines that sensed coordinate vector is not within upright posture cone 154, posture state module 46 detects that patient 12 is not in the upright posture.

Posture state module 46 may analyze the sensed coordinate vector in posture state space 152 with respect to each individual defined posture cone, such as posture cones 156 and 158, in such a manner to determine the posture state of patient 12. For example, posture state module 46 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 46 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 46 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 46 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 46 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 46 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 46 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 46 may then determine the particular lying posture state occupied by patient 12, e.g., lying front, lying back, lying right, or lying left. To determine the particular lying posture state occupied by patient 12, posture state module 46 may analyze the sensed vector with respect to reference coordinate vectors for individual lying posture state cones, e.g., lying front cone 156, lying back cone 158, lying right cone (not shown), and lying left cone (not shown), using one or more techniques previously described, such as angle or cosine techniques. For example, posture state module 46 may determine whether the sensed coordinated vector resides within one of the lying posture state cones and, if so, select the posture state corresponding to that cone as the detected posture state.

FIG. 6C illustrates an example posture state space 155 that is a three-dimensional space substantially similar to posture state space 152 of FIG. 6B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 6C illustrates a method for detecting a lying posture based on proximity of a sensed coordinate vector to one of the reference coordinate vectors for the lying postures.

As shown in FIG. 6C, posture state space 155 includes four reference coordinate vectors 159, 161, 163, 165, which are associated with lying left, lying right, lying front, and lying back posture states, respectively. Posture state module 46 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 6B, the posture state reference data (i.e., one or more posture state definitions) for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 6B) or cosine values with respect to upright posture reference coordinate vector 167, in which case posture state module 46 may determine that patient 12 is in a general lying posture state.

If posture state module 46 determines that patient 12 is occupying a general lying posture state, posture state module 46 may then calculate the cosine value of the sensed coordinate vector with respect to each lying reference coordinate vectors 159, 161, 163, 165. In such a case, posture state module 46 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 46 may determine that patient 12 is occupying a lying front posture state.

In some examples, posture state module 46 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 6B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 46 may compute the cross-products of various combinations of lying reference vectors 159, 161, 163, 165 and average the cross product values. In the example of FIG. 6C, posture state module 46 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 46 may define a lying posture donut or toroid in a manner similar to that described with respect to upright reference vector 167, but instead with respect to virtual upright reference vector 169. In particular, when posture state module 46 determines that the patient is not in the upright posture, the posture state module determines whether the patient is in a lying posture based on an angle or cosine value with respect to the virtual upright reference vector 169.

Posture state module 46 may still determine whether patient 12 is in an upright posture state using upright posture cone 157. If posture state module 46 determines that patient 12 is occupying a general lying posture state based on the analysis of the sensed coordinate vector with respect to virtual upright reference vector 169, posture state module 46 may then calculate the cosine value of the sensed coordinate vector (as hypotenuse) with respect to each lying reference coordinate vectors 159, 161, 163, 165 (as adjacent).

In such a case, posture state module 46 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 6B and 6C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

A clinician may orient one or more sensors of posture state module 46. For example, as prompted by clinician programmer 60, a clinician may instruct patient 12 to occupy a specified posture, e.g., standing, so that posture state module 46 may sense a reference coordinate vector for the respective posture. The clinician may provide an indication that patient 12 is in the specified posture. In response to the indication from the clinician, a vector measured by posture state module 46 may be stored, e.g., in memory 42 of IMD 14, as a reference coordinate vector. The clinician may repeat this process with various specified postures, e.g., lying back or lying front and lying left or lying right. The orientation process may yield a set of reference coordinate vectors. These posture state reference coordinate vectors may be associated with posture state definitions and used to classify the posture of patient 12 within a posture state. In some cases, the reference coordinate vectors may be used by one or more posture state definitions to define respective postures in space. In this manner, each posture statue definition for a posture may include at least one reference coordinate vector that at least partially defines the posture. If a reference vector is used to device an edge of a posture in space, several posture state definitions may be associated with the same reference coordinate vector.

As described with respect to FIGS. 6A-6C, a posture state may be defined by a posture state reference coordinate vector and a tolerance, e.g., angle, cosine, or distance value. The reference coordinate vector and a tolerance for a posture state are examples of posture state reference data and a posture state definition. Each of these aspects may be parameters of a set of posture state definitions. Moreover, each of the parameters may be adjusted to calibrate the posture state module to the particular orientation of the sensors within the patient and/or typical patient postures. These postures may also change over time and require updating periodically. Programmer 20 may prompt the clinician to orient one or more sensors of posture state module 46 to establish values for one or more posture state reference coordinate vectors associated with posture state definitions. Once values for the posture state reference coordinate vectors associated with the posture state definitions have been established, posture state module 46 is enabled to classify the posture state of patient 12 according to the set of posture state definitions. In this manner, the only user input required to enable the set of posture state definitions for posture responsive therapy may be the indications received during the orientation procedure. The values for the posture state reference coordinate vectors established during the orientation process are input into the pre-established posture state definitions.

In addition, the methods for defining a posture state described with respect to FIGS. 6A-6C may include the ability to define activity or mobility in addition to the other stationary orientations of patient 12. A mobility posture state may be a specific posture state defined only on movement of patient 12 or a combination of movement and a stationary orientation of patient 12. For example, a mobility posture state may only be determined when the patient 12 is already detected within a standing or upright posture state. In this example, the set of posture state definitions may require that the standing or upright posture state is detected and motion of patient 12 is detected to exceed a mobility threshold, such as, e.g., a threshold representing a number of movements (such as walking or jogging steps) in a given time period. In other examples, a mobility posture state may be determined for any posture or orientation also detected when the activity or mobility of patient 12 is detected to exceed the mobility threshold.

Posture state module 46, or any other module tasked with detecting mobility, may use an algorithm to detect the mobility posture state (e.g., when a level of activity or motion has been detected). In some examples, this level may be defined by a mobility threshold that represents a magnitude and/or duration that activity was detected. For example, posture state module 46 may determine that the mobility threshold has been exceeded when a certain number of oscillations greater than a predetermined magnitude occur within a predetermined period of time. In other examples, the number of oscillations may need to exceed a predetermined magnitude and a predetermined frequency for a certain period of time. These algorithms may also be modified to incorporate rolling averages, moving windows of time, weighted average of magnitudes, or any other methods of determining when the motion of the patient should be considered to have exceeded the mobility threshold. In this manner, the mobility threshold may be a simple value or a complex sensitivity to detected motion that triggers determination of the mobility posture state.

Figure 7:
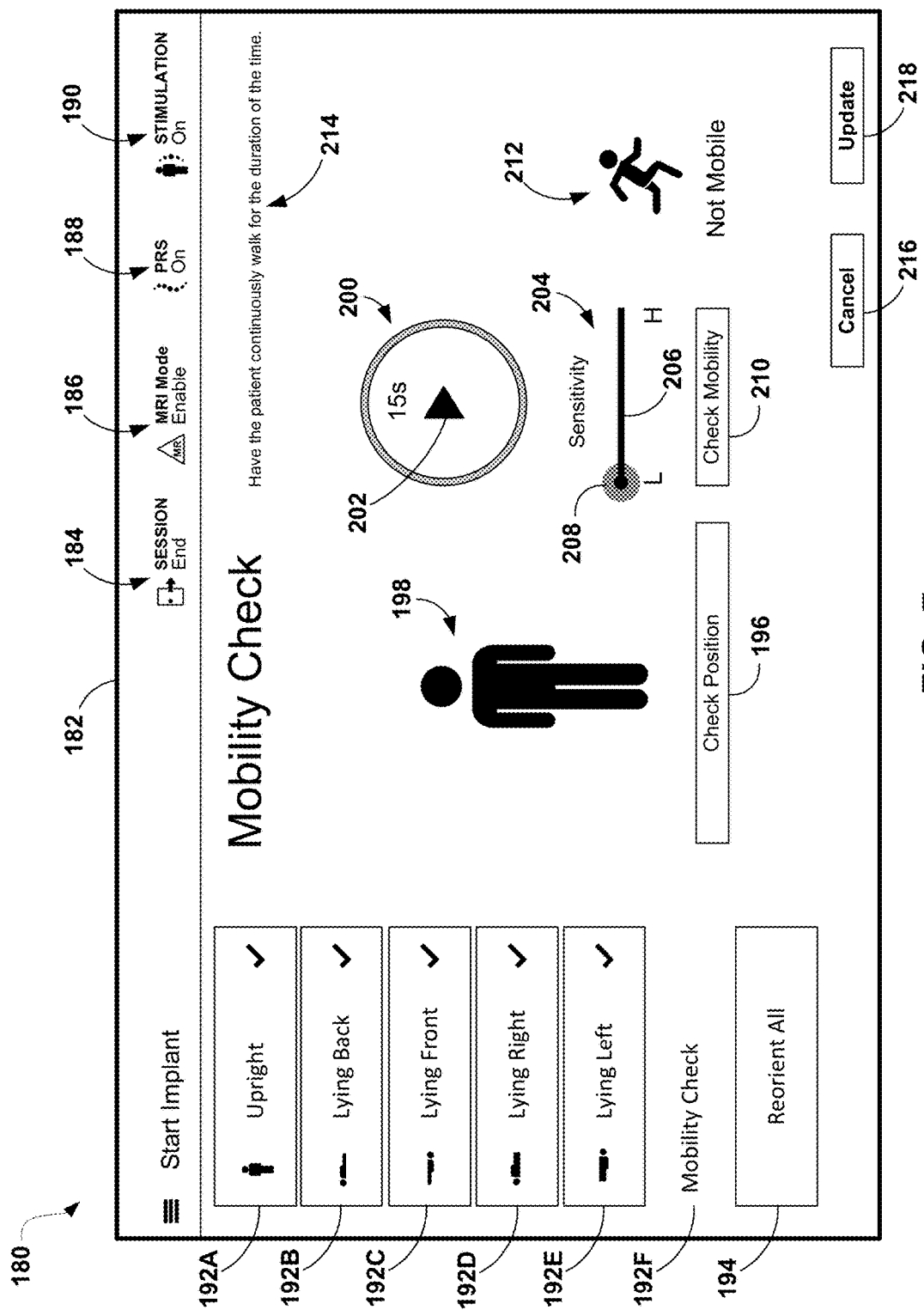
FIG. 7 is a conceptual diagram illustrating an example user interface of an external programmer for adjusting a parameter of a posture state definition.

FIG. 7 is a conceptual diagram illustrating an example user interface 180 of an external programmer 20 for adjusting a parameter of a posture state definition. User interface 180 may be an example of user interface 66 of programmer 20 in some examples. Although user interface 180 may typically be used for a clinician programmer and used by a clinician, user interface 180, alternatively or additionally, may be presented in a patient programmer in other examples. Moreover, user interface 180 is generally described as being presented via a touchscreen device. However, one or more features of user interface 180 may be implemented with one or more inputs having switches, dials, slides, buttons, keypads, or any other mechanisms separate from a touchscreen display.

As shown in the example of FIG. 7, user interface 66 of programmer 20 may provide example user interface 180 to the user, such as a clinician, via screen 182. User interface 180 may relate to a "Mobility Check" screen that includes features for calibrating the detection of posture states by IMD 14, for example. Although screen 182 is shown for the example of calibrating the mobility posture state, variations of screen 182 may be used to calibrate other posture states such as upright, lying back, lying front, lying right, lying left, or other posture states. Screen 182 includes session end button 184, MRI Mode toggle 186, posture responsive therapy toggle 188, and stimulation therapy toggle 190. Screen 182 also includes posture state icons 192A-192F (collectively "posture state icons 192"), reorient button 194, instruction field 214, timer 200, determined posture state icon 198, check position button 196, mobility threshold 204, check mobility button 210, mobility indicator 212, cancel button 216, and update button 218.

Session end button 184 may, when selected by a user, end the calibration session of the posture state module 46 of IMD 14. MRI Mode toggle 186 switches the operating mode of IMD 14 between an enabled mode (e.g., safe for IMD 14 to be placed in an MRI device) and disabled mode (e.g., IMD 14 should not be placed within an MRI device). Posture responsive therapy toggle 188 switches between making the delivery of therapy responsive to detected posture states (e.g., PRS On) and making the delivery of therapy independent or not responsive to detected posture states. Stimulation therapy toggle 190 switches between instructing IMD 14 to deliver therapy to turning therapy off.

Posture state icons 192 provide different indications of whether the respective posture states have been calibrated or not. A check mark is provided for those posture states that have been calibrated, as shown for each of posture state icons 192A-192E in FIG. 7. A check mark is not provided for posture state icon 192F because the mobility posture state has not yet been calibrated. In some examples, each of posture state icons 192 may be selectable such that selection of one of the posture state icons 192 navigates user interface 180 to the screen in which that particular posture state can be calibrated. Selection of reorient button 194 may, when selected, reset all of the calibrations for each posture state and/or guide the user back through the calibration process for each posture state.

Screen 182 also provides features for checking and adjusting aspects of the mobility posture state. User selection of check position button 196 may cause programmer 20 to interrogate IMD 14 to retrieve the current detected posture state. Upon receiving the detected posture state from IMD 14, programmer 20 may update determined posture state icon 198 to reflect the detected posture state from IMD 14. As shown in FIG. 7, determined posture state icon 198 indicates an upright posture. Determined posture state icon 198 may reflect those posture states representative of an orientation of the patient. In other words, mobility or activity of the patient may not be reflected by determined posture state icon 198. Instead, the mobility or activity of patient 12 may be represented by mobility indicator 212 instead. In this manner, screen 182 may show the orientation and mobility as separate elements of a posture state such that mobility is determined in addition to whether or not patient 12 is upright (or another posture state in other examples). In other examples, determined posture state icon 198 may show mobile posture states as well as the other orientation type posture states (e.g., the posture states of posture state icons 192A-192E).

To check or calibrate the mobility posture state for patient 12, the user may select check mobility button 210. Upon selecting check mobility button 210, programmer 20 may transmit a request for IMD 14 to start generating data representative of patient 12 for determining the posture state assumed by the patient over a period of time. Timer 200 may begin counting down to present the remaining time required for IMD 14 to monitor the patient posture and determine which posture state is being assumed. In the example of FIG. 7, the period of time is 15 seconds. However, shorter or longer periods of time may be used in other examples (e.g., 30 seconds or 60 seconds). The period of time may be selected by the user via screen 182. Longer periods of time may lead to more robust calibration of the posture state in some examples. For the period of time, instruction field 214 may tell the user what to do. In this example, instruction field 214 may instruct the user to "Have the patient continually walk for the duration of the time." This instruction would lead to patient 12 walking and thus assuming the mobile posture state during the period of time.

While IMD 14 is generating posture data, programmer 20 may operate timer 200 and show the number of seconds remaining for the period of time. In some examples, timer 200 may also include a ring that increases or decreases the shading of the ring to track the elapsed or remaining duration of the period of time, respectively. Status icon 202 may indicate whether the mobility check is currently in process (e.g., IMD 14 is generating posture data to determine the assumed posture state). A triangle of status icon 202 may be shown to indicate that no process is currently occurring, and two vertical bars of status icon 202 may be shown to indicate that IMD 14 is currently monitoring posture. In some examples, status icon 202 may be selectable such that the user can start and/or pause the mobility check directly from timer 200.

After timer 200 shows that the period of time has expired, IMD 14 may automatically, or in response to a request from programmer 20, transmit the determined posture state for the period of time and/or the generated posture data. If IMD 14 transmits the generated data, IMD 14 may also transmit the set of posture state definitions, or at least some of the definitions related to the mobility posture state. Programmer 20 may then update mobility indicator 212 to reflect whether or not the posture state definitions led to the determination of the mobility posture state for the posture data generated during the period of time. It is noted that the mobility threshold of the set of posture state definitions may be initially set to a default value for patient 12. The default value may be the lowest or least sensitive value to movement of patient 12. This lowest value may require the clinician to explicitly calibrate the mobility threshold to the patient because the mobile posture state may not be determined with the default threshold value. Alternatively, the default value may be set to a value according to the patient condition, age, demographic, activity level, previous medical device trial data, patient answers to a questionnaire, or any other factor for predicting the appropriate threshold value.

Mobility threshold 204 may provide functionality for the user to correct the mobility threshold (e.g., a parameter of the set of posture state definitions) if mobility indicator 212 does not reflect the posture state actually assumed by patient 12 during the period of time. Mobility threshold 204 may be an adjustment mechanism for adjusting the threshold defining the mobility posture state. The user may select slider 208 and move slider 208 within adjustment range 206 to make the threshold more sensitive to patient movement or less sensitive to patient movement.

When the user releases slider 208, programmer 20 may obtain the updated posture state that would have been determined from the posture data generated during the period of time and the updated set of posture state definitions including the new mobility threshold value. If the updated posture state would now be the mobile posture state, programmer 20 may show that the user is "mobile" in mobility indicator 212. If the updated posture state is the same as before, mobility indicator 212 would not change. Programmer 20 may obtain the updated posture state by interrogating IMD 14 (e.g., transmitting the updated mobility threshold value to IMD 14 and receiving the newly determined posture state from IMD 14). Alternatively, programmer 20 may determine the updated posture state by applying the generated posture data to the updated set of posture state definitions. In this manner, programmer 20 may not need to interrogate IMD 14 after each adjustment to the mobility threshold.

In other examples, programmer 20 may provide "live" or real-time updates to the posture state as the user adjusts the mobility threshold 204. In other words, as the user moves slider 208 to move through different values of the mobility threshold, programmer 20 may responsively re-calculate the updated posture state with the generated posture data and the updated set of posture state definitions. Screen 182 may thus immediately reflect the updated posture state as the user moves slider 208. This approach may allow the user to quickly identify the threshold value at which the mobility posture state would have been determined for patient 12 using the previously generated posture data. Programmer 20 may independently determine the updated posture state by applying the adjusted mobility threshold to previously generated posture data received from IMD 14. In other examples, programmer 20 may interrogate IMD 14 one or more times during movement of slider 208, to receive the updated posture states corresponding to the adjusted mobility threshold. In other words, programmer 20 may perform repeated interrogations as the slider is moved to the respective increment. The interrogations may be temporally fixed (e.g., a temporal interrogation rate such as a predetermined number of interrogations per second) or temporally dynamic (e.g., an interrogation is performed for each predetermined increment in the mobility threshold or the interrogation rate is based on the speed with which slider 208 is moved such that slower movement of slider 208 results less frequent interrogations and faster movement results in more frequent interrogations).

In some examples, programmer 20 may provide a suggested threshold value to the user instead of the user needing to manually adjust the threshold using slider 208. For example, screen 182 may include a "suggested threshold" button to select the suggested value at which the threshold can be set so that the mobile posture state would be determined for the generated posture data. In other words, programmer 20 and/or IMD 14 may analyze the generated posture data and determine which parameter values of the set of posture state definitions would have resulted in the determination of the mobile posture state. In some examples, the suggested threshold may be the minimal threshold or least sensitive threshold value that would result in the determination of the mobile posture state. In other examples, the suggested threshold may be set above the minimum threshold value with an error factor or other margin of error such that the mobile posture state will be detected. The error factor may be a predetermined percentage or value or a value determined from the particular posture data generated for patient 12. In some examples, selection of the suggested threshold value may cause programmer 20 to set the slider to the appropriate value on adjustment range 206. Programmer 20 may subsequently allow the user to also manually move slider 208 from the suggested value for further adjustment of the mobility threshold 204.

Once the user is satisfied with the threshold value selected from mobility threshold 204, the user may select the update button 218. Update button 218 may trigger the updated set of posture state definitions (including the updated mobility threshold) to be stored and transmitted to IMD 14 for use in determine posture states for patient 12. Selection of cancel button 216 may cause programmer 20 to discard the updates to the posture state definitions and cancel any changes.

Screen 182 shows the adjustment of a single threshold as one parameter of the set of posture state definitions. However, in other examples, screen 182 may provide multiple different thresholds to be adjusted on the same screen. For example, the mobility posture state may be split into two or more mobility posture states (e.g., low, medium, and high mobility). Each of these mobility posture states may be bounded by a respective threshold. Each of these thresholds may have a respective adjustment mechanism similar to mobility threshold 204 in this example. Although mobility threshold 204 is described for defining a mobile posture state, similar adjustment mechanism may be provided to adjust parameters related to other posture states such as the posture states of posture state icons 192. In some examples, multiple posture states may be adjusted on a single screen of user interface 180.

As described herein, system 10 is configured to facilitate the adjustment of the set of posture state definitions that are used to determine the posture state of patient 12. In one example, programmer 20 may be configured to present an indication of a first posture state determined from data representative of a patient posture during a period of time and a set of posture state definitions that at least partially define a plurality of posture states, wherein the first posture state is one posture state of the plurality of posture states. Programmer 20 may also receive an adjustment input from a user that requests an adjustment to the set of posture state definitions. Programmer 20 may then obtain a second posture state determined from the data representative of the patient posture during the period of time and the adjusted set of posture state definitions and presenting an indication of the second posture state (e.g., mobility indication 212). In some examples, the second posture state that is determined may be an indication that the patient is not in the first posture state.

Programmer 20 may be configured to transmit a request to IMD 14 to generate the data representative of the patient posture during the period of time. IMD 14 may generate this posture data with a sensor such as included in posture state module 46, for example. Programmer 20 may also present timer 200 that tracks the period of time during which patient 12 assumes the patient posture. Upon expiration of the period of time, or responsive to determining that the period of time has expired, programmer 20 may obtain the first posture data determined from data representative of a patient posture during a period of time.

Programmer 20 may obtain the second, or updated, posture state by applying the data representative of the patient posture during the period of time to the adjusted set of posture state definitions. Alternatively, programmer 20 may obtain the updated posture state by transmitting, to IMD 14, the adjusted set of posture state definitions and receiving, from IMD 14, the updated posture state determined by IMD 14 from the data representative of the patient posture during the period of time and the adjusted set of posture state definitions.

In some examples, programmer 20 may perform an iterative process to provide updated posture states in response to detecting user adjustments to mobility threshold 204. This iterative process may proceed for each incremental adjustment input received via slider 208 or as a "live update" as the user adjusts the mobility threshold in real time. Programmer 20 may thus provide the "live update" by recalculating the posture state in real-time using the changing mobility threshold and applying it to the previously generated data representative of the patient posture during the period of time. For example, programmer 20 may be configured to receive repeated adjustment inputs from the user that request respective adjustments to the set of posture state definitions (e.g., adjustments to the mobility threshold via a slider or dial) and, responsive to receiving each adjustment input of the repeated adjustment inputs, obtain intermediate posture states determined from the data representative of the patient posture during the period of time and the respective adjusted sets of posture state definitions. Programmer 20 may, responsive to obtaining each of the intermediate posture states for each adjustment input of the repeated adjustment inputs, present, via user interface 180 and mobility indication 212, respective indications of the intermediate posture states.

As discussed above, user interface 180 may present an adjustment mechanism (e.g., mobility threshold 204) configured to adjust, upon receiving the adjustment input from the user, one parameter of the set of posture state definitions instead of other parameters of the set of posture state definitions. Thus, the adjustment input does not merely select or replace an entirely new posture state definition. Instead, the mobility threshold may be the only parameter that is adjusted from the posture state definition in some examples. The mobility threshold may be associated with only one posture (e.g., only the upright posture), or the mobility threshold may associated with multiple or all postures (e.g., to indicate mobility regardless of which static posture is detected). The adjustment mechanism may include slider 208 that is movable by the adjustment input from the user to a position within adjustment range 206 of the one parameter. Other types of adjustment mechanisms may be used in other examples, such as a dial, scroll wheel, arrow inputs, numerical input, or other mechanisms. The one parameter that is adjusted via mobility threshold 204 may be a threshold defining the mobile posture state of the plurality of posture states. In addition, the mobility threshold may be a set of two or more thresholds in other examples, where each of the thresholds indicates a different magnitude of mobility for the patient (e.g., one threshold for walking, one threshold for running, and one threshold for biking).

The example plurality of posture states may include at least one of an upright posture state, a lying back posture state, a lying front posture state, a lying right posture state, a lying left posture state, and a mobile posture state. Other posture states may be included or not included in this list. The mobile posture state may be a fully independent posture state. In other examples, the mobile posture state may be a combination of a stationary posture state or orientation of the patient and a detected activity or mobility level exceeding one or more thresholds. As discussed herein, the determination of posture states may be used by IMD 14 to provide posture responsive therapy. For example, programmer 20 may control IMD 14 to deliver posture responsive therapy to patient 14 based on the adjusted set of posture state definitions (e.g., programmer 20 may transmit updated posture state definitions to IMD 14 for use in delivering therapy).

Figure 8:
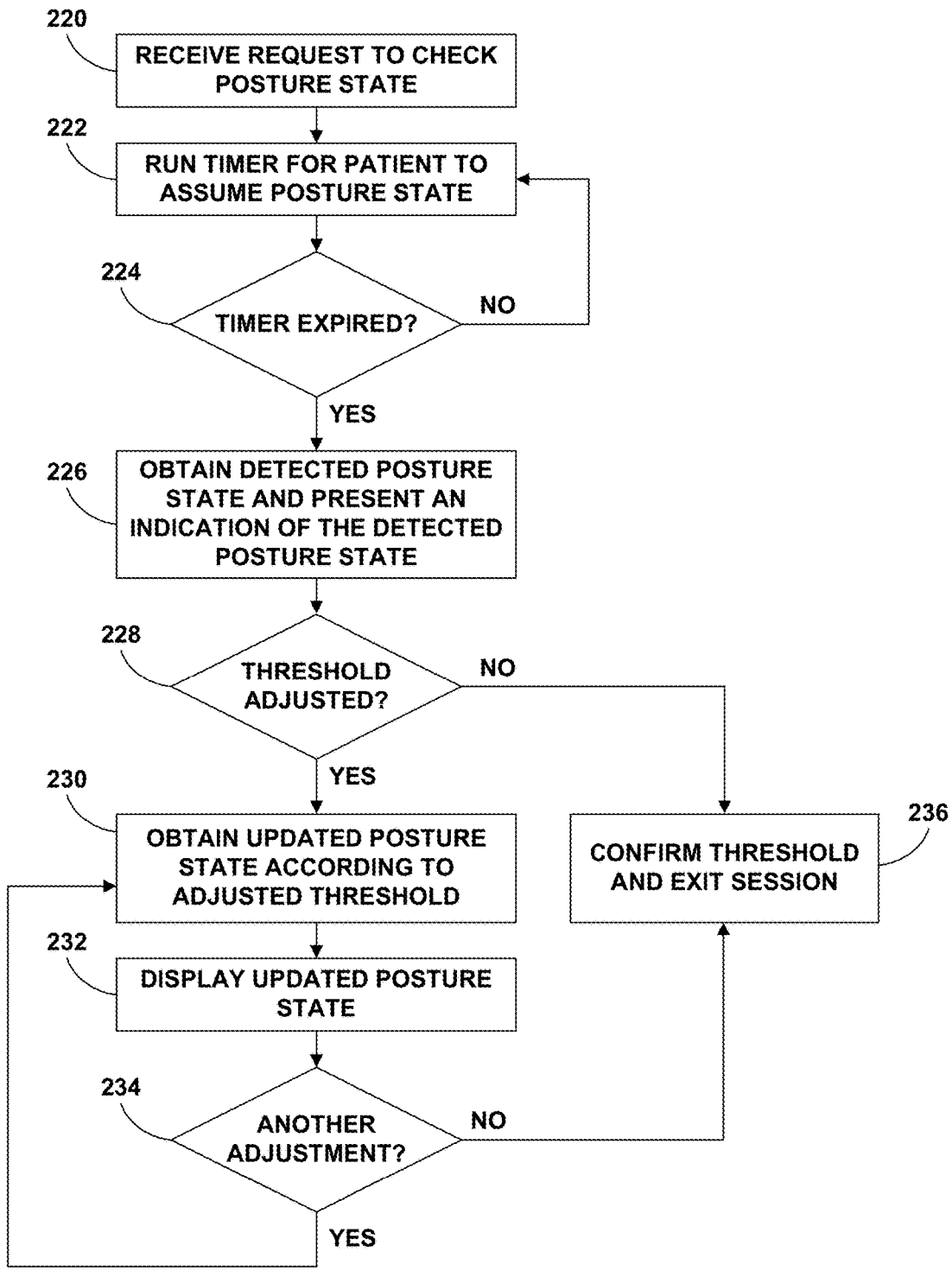
FIG. 8 is a flow diagram illustrating an example method for adjusting a parameter of a set of posture state definitions and updating the determined posture state.

FIG. 8 is a flow diagram illustrating an example method for adjusting a parameter of a set of posture state definitions and updating the determined posture state. The example of FIG. 8 will be described with respect to processor 64 of external programmer 20 and IMD 14. However, these processes may be at least partially completed by other devices such as processor 40 of IMD 14, server 82, and/or computing devices 84, in other examples.

As shown in FIG. 8, processor 64 may receive, via user interface 66, a request from a user to check the posture state of a patient (220). For example, the posture state check may be to check the mobility threshold that at least partially defines the mobility posture state. Processor 64 may transmit the request to IMD 14 to generate posture data and run a timer for the patient to assume the intended posture state (222). For example, the user may instruct the patient to walk for the duration of the period of time tracked by the timer in order for IMD 14 to determine whether or not a mobile posture state is detected. If the timer has not expired ("NO" branch of block 224), processor 64 may continue to run the timer. If the timer has expired ("YES" branch of block 224) processor 64 may obtain the detected posture state and present the indication of the detected posture state via user interface 66 (226). Processor 64 may interrogate IMD 14 to retrieve the determined posture state.

User interface 66 of programmer 20 may show the indication of the detected posture state so that the user can determine if the detected posture state is an accurate representation of the posture state actually assumed by the patient. User interface 66 may allow the user to adjust the set of posture state definitions if the determined posture state is not accurate (e.g., adjust mobility threshold 204). If processor 64 determines the user has not adjusted a threshold (e.g., via canceling the process or confirming the current posture state definitions) ("NO" branch of block 228), processor 64 may confirm the threshold of the set of posture state definitions and exit the adjustment session (236).

If processor 64 receives an adjustment to the threshold ("YES" branch of block 228), processor 64 may use the adjusted threshold (e.g., a changed value of a mobility threshold) to obtain an updated posture state according to the adjusted threshold and the previously generated posture data from the period of time (230). Processor 64 may then display an indication (e.g., an icon) of the updated posture state (232). If processor 64 receives another adjustment to the threshold ("YES" branch of block 234), processor 64 may again obtain a newly updated posture state (230). If processor 64 does not receive another adjustment to the threshold ("NO" branch of block 234), processor 64 may confirm the latest threshold for the set of posture state definitions and exit the adjustment session (236).

Figure 9:
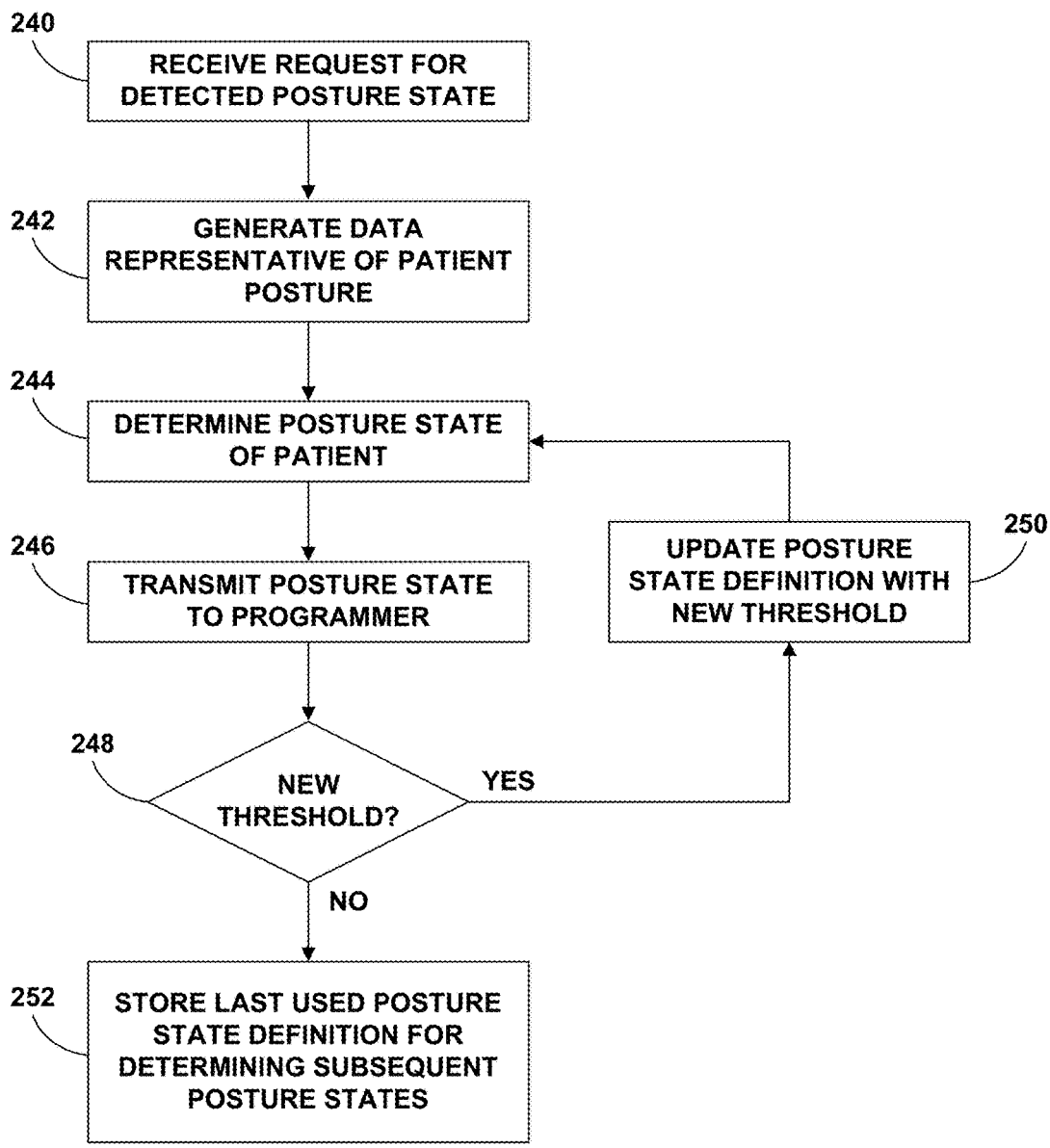
FIG. 9 is a flow diagram illustrating an example method for updating the determined posture state with an adjusted set of posture state definitions.

FIG. 9 is a flow diagram illustrating an example method for updating the determined posture state with an adjusted set of posture state definitions. The example of FIG. 9 will be described with respect to processor 40 of IMD 14. However, these processes may be at least partially completed by other devices such as processor 64 of programmer 20, server 82, and/or computing devices 84, in other examples.

As shown in FIG. 9, processor 40 may receive a request for a detected posture state (240). Processor 40 may initiate posture detection by posture state module 46 and generate data representative of patient posture (242). For example, the generated data may be posture data that includes output from one or more accelerometers, gyroscopes, or other sensors. Processor 40 may then determine the posture state of the patient based on the generated posture data and the stored set of posture state definitions (244). In some examples, posture state module 46 may determine the posture state. Processor 40 may then transmit the determined posture state to programmer 20 for presentation to the user (246).

If processor 40 receives a new or updated threshold value ("YES" branch of block 248), processor 40 may update the set of posture state definitions with the new threshold value (e.g., a new mobility threshold value) (250) and again determine the posture state using the updated set of posture state definitions and the previously generated posture state (244). Processor 40 may continue this process as long as programmer 40 transmits new threshold values. If processor 40 no longer receives new thresholds ("NO" branch of block 248), processor 40 may store the latest used posture state definitions for use in determining subsequent posture states (252). Processor 40 may use the posture state definitions to track posture states and provide posture responsive therapy in some examples.

As discussed above, according to one alternative, IMD 14 may instead transfer posture data to programmer 20. Processor 64 of programmer 20 may determine the posture state based on the posture state data and the posture state definitions. As new or updated threshold values are received from the user, processor 64 of programmer 20 may update the posture state definitions and determine the posture states based on the previously-received posture state data and the new threshold values for the posture state definitions.

In addition, it should be noted that system 10 or other systems and devices described herein may not be limited to treatment or monitoring of a human patient. In alternative examples, system 10 may be implemented in non-human patients, e.g., primates, canines, equines, pigs, and felines. These other animals may undergo clinical or research therapies that may benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
presenting, by a user interface of a programmer for an implantable medical device (IMD), an indication of a first posture state determined from data representative of a patient posture during a period of time and a set of posture state definitions that at least partially define a plurality of posture states, wherein the first posture state is one posture state of the plurality of posture states;
receiving, by a processor of the programmer, an adjustment input from a user that requests an adjustment to the set of posture state definitions to update the first posture state to a second posture state;
obtaining, by the processor of the programmer, the second posture state, the second posture state determined from the data representative of the patient posture during the period of time and the adjusted set of posture state definitions; and
presenting, by the user interface of the programmer, an indication of the second posture state.

2. The method of claim 1, wherein obtaining the second posture state comprises determining, by the programmer, the second posture state by applying the data representative of the patient posture during the period of time to the adjusted set of posture state definitions.

3. The method of claim 1, wherein obtaining the second posture state comprises:
transmitting, to the IMD, the adjusted set of posture state definitions; and
receiving, from the IMD, the second posture state determined by the IMD, the second posture state determined from the data representative of the patient posture during the period of time and the adjusted set of posture state definitions.

4. The method of claim 1, further comprising:
transmitting, by the programmer, a request to the IMD to generate the data representative of the patient posture during the period of time;
presenting, by the programmer, a timer that tracks the period of time during which the patient assumes the patient posture; and
upon expiration of the period of time, obtaining the first posture data determined from data representative of a patient posture during a period of time.

5. The method of claim 1, wherein the first posture state is different from the second posture state.

6. The method of claim 1, wherein the first posture state is the same as the second posture state.

7. The method of claim 1, wherein:
receiving the adjustment input comprises receiving, by the programmer, repeated adjustment inputs from the user that request respective adjustments to the set of posture state definitions,
obtaining the second posture state comprises, responsive to receiving each adjustment input of the repeated adjustment inputs, obtaining, by the programmer, intermediate posture states determined from the data representative of the patient posture during the period of time and the respective adjusted sets of posture state definitions, and
wherein the method comprises, responsive to obtaining each of the intermediate posture states for each adjustment input of the repeated adjustment inputs, presenting, by the user interface of the programmer, respective indications of the intermediate posture states.

8. The method of claim 1, further comprising presenting, by the user interface of the programmer, an adjustment mechanism configured to adjust, upon receiving the adjustment input from the user, one parameter of the set of posture state definitions instead of other parameters of the set of posture state definitions.

9. The method of claim 8, wherein the adjustment mechanism comprises a slider movable by the adjustment input to a position within an adjustment range of the one parameter.

10. The method of claim 8, wherein the one parameter comprises a threshold defining a mobile posture state of the plurality of posture states, at least one of the first posture state or the second posture state being the mobile posture state.

11. The method of claim 1, wherein the plurality of posture states comprise an upright posture state, a lying back posture state, a lying front posture state, a lying right posture state, a lying left posture state, a reclining back posture, and a mobile posture state.

12. The method of claim 1, further comprising controlling, by the programmer, the IMD to deliver posture responsive therapy to the patient based on the adjusted set of posture state definitions.

13. The method of claim 12, wherein controlling the IMD to deliver posture responsive therapy comprises controlling the IMD to deliver electrical stimulation therapy to the patient.

14. An external programmer for programming an implantable medical device (IMD), the external programmer comprising:
a user interface configured to present an indication of a first posture state determined from data representative of a patient posture during a period of time and a set of posture state definitions that at least partially define a plurality of posture states, wherein the first posture state is one posture state of the plurality of posture states; and
a processor configured to:
receive an adjustment input from a user that requests an adjustment to the set of posture state definitions to update the first posture state to a second posture state; and obtain the second posture state, the second posture state determined from the data representative of the patient posture during the period of time and the adjusted set of posture state definitions, wherein the user interface is configured to present an indication of the second posture state.

15. The external programmer of claim 14, wherein the processor is configured to determining the second posture state by applying the data representative of the patient posture during the period of time to the adjusted set of posture state definitions.

16. The external programmer of claim 14, further comprising a telemetry circuit, wherein the processor is configured to obtain the second posture state by:
transmitting, to the IMD via the telemetry circuit, the adjusted set of posture state definitions; and
receiving, from the IMD via the telemetry circuit, the second posture state determined by the IMD, the second posture state determined from the data representative of the patient posture during the period of time and the adjusted set of posture state definitions.

17. The external programmer of claim 14, wherein the first posture state is one of different from or the same as the second posture state.

18. The external programmer of claim 14, wherein the processor is configured to:
receive repeated adjustment inputs from the user that request respective adjustments to the set of posture state definitions;
responsive to receiving each adjustment input of the repeated adjustment inputs, obtain intermediate posture states determined from the data representative of the patient posture during the period of time and the respective adjusted sets of posture state definitions; and
control the user interface to, responsive to obtaining each of the intermediate posture states for each adjustment input of the repeated adjustment inputs, present respective indications of the intermediate posture states.

19. The external programmer of claim 14, wherein the user interface is configured to present an adjustment mechanism configured to adjust, upon receiving the adjustment input from the user, one parameter of the set of posture state definitions instead of other parameters of the set of posture state definitions.

20. The external programmer of claim 19, wherein the one parameter comprises a threshold defining a mobile posture state of the plurality of posture states, at least one of the first posture state or the second posture state being the mobile posture state, and wherein the plurality of posture states comprise an upright posture state, a lying back posture state, a lying front posture state, a lying right posture state, a lying left posture state, and the mobile posture state.

21. The external programmer of claim 14, wherein the processor is configured to control the IMD to deliver electrical stimulation therapy to the patient, wherein the electrical stimulation therapy is adjusted in response to posture state changes of the patient.

22. A system comprising:
an implantable medical device (IMD) comprising one or more posture sensors configured to generate data representative of a patient posture during a period of time; and
an external programmer for programming the IMD, the external programmer comprising:
a user interface configured to present an indication of a first posture state determined from the data representative of the patient posture state during the period of time and a set of posture state definitions that at least partially define a plurality of posture states, wherein the first posture state is one posture state of the plurality of posture states; and
a processor configured to:
receive an adjustment input from a user that requests an adjustment to the set of posture state definitions to update the first posture state to a second posture state; and
obtain the second posture state, the second posture state determined from the data representative of the patient posture during the period of time and the adjusted set of posture state definitions, wherein the user interface is configured to present an indication of the second posture state.

23. The system of claim 22, wherein the IMD is configured to deliver electrical stimulation therapy to the patient, and wherein the electrical stimulation therapy is adjusted in response to posture state changes of the patient.

* * * * *